United States Patent
Lin (10) Patent No.: US 6,992,488 B2
(45) Date of Patent: Jan. 31, 2006

(54) SELF-CLEANING PROBE SYSTEM

(75) Inventor: Shawn H. Lin, Atlanta, GA (US)

(73) Assignee: BioLab Services, Inc., Wilmington, DE (US)

(*) Notice: Subject to any disclaimer, the term of this patent is extended or adjusted under 35 U.S.C. 154(b) by 0 days.

(21) Appl. No.: 10/221,393

(22) PCT Filed: Jun. 4, 2002

(86) PCT No.: PCT/US02/17445

§ 371 (c)(1),
(2), (4) Date: Sep. 12, 2002

(87) PCT Pub. No.: WO02/101400

PCT Pub. Date: Dec. 19, 2002

(65) Prior Publication Data

US 2003/0183538 A1 Oct. 2, 2003

(51) Int. Cl.
*G01N 27/416* (2006.01)

(52) U.S. Cl. ........................................... 324/438
(58) Field of Classification Search ................. 324/518, 324/438, 439, 754
See application file for complete search history.

(56) References Cited

U.S. PATENT DOCUMENTS

| | | |
|---|---|---|
| 4,329,649 A | 5/1982 | Scoates |
| 4,752,740 A | 6/1988 | Steininger |
| 5,132,017 A | 7/1992 | Birdsong et al. |
| 5,342,510 A | 8/1994 | Eden et al. |
| 5,484,549 A * | 1/1996 | Hei et al. ................ 510/370 |
| 5,760,371 A * | 6/1998 | Dailey et al. ............ 219/129 |
| 6,078,178 A | 6/2000 | Barnett |

OTHER PUBLICATIONS

ORP Control in Pools and Spas, Dr. J. Steininger D. Sc.; Santa Barbara Controls Systems, Copyright SBCS 1998.
ORP Testing and Chemical Automation for Swimming Pools and Spas, Jacques M. Steininger, D. Sc.; Santa Barbara Controls Systems, Copyright SBCS 1990.
Analytical and Control Techniques for Chlorine and Hypochlorite, TREYTEC, Inc., Jun. 1996; Water Treatment Technology Newsletter.
Model 223 Ultrasonic Cleaners, Technology for Solutions, GLI International, (no date).
B15/72 Auto–Clean pH/ORP Monitor, Analytical Technology, Inc., May 2001.
Reduction–Oxidation Measurements, Sensorex, May 2001.

* cited by examiner

Primary Examiner—N. Le
Assistant Examiner—Amy He
(74) Attorney, Agent, or Firm—Smith, Gambrell & Ru (57) ABSTRACT

A self-cleaning oxidation-reduction potential ("ORP") probe system includes an ORP electrode (11), a flow cell (12) surrounding the ORP electrode, and a plurality of cleaning beads (17) contained in the flow cell in a manner in which they are free to contact the ORP electrode when fluid is passed through the flow cell. The self-cleaning probe system may also or alternatively include a pH probe electrode, or another fluid-testing probe, in the flow cell.

12 Claims, 15 Drawing Sheets

SELF-CLEANING PROBE SYSTEM

FIELD OF THE INVENTION

The present invention relates generally to probes for determining oxidation-reduction potential ("ORP") and/or pH, and more particularly to a self-cleaning ORP and/or pH probe system.

BACKGROUND OF THE INVENTION

Water used in circulating water systems (such as, for example, swimming pools or other recreational water systems) is commonly treated with a halogenated sanitizer to kill and control the growth of bacteria, viruses, algae, etc. A minimum level of sanitizer residual is commonly maintained in such systems to kill potentially pathogenic bacteria that may be introduced into the system. For example, sanitizer manufacturers and the federal government require within approved label directions for all chlorine and bromine based sanitizers that a halogen residual be maintained and be measured by an appropriate chemical method for "chlorine" or "bromine."

To better operate pools and spas, automatic chemical feeders and automatic controllers may be used. The controllers are designed to feed chemicals either on a timer basis, or based on the chemical properties of the water. The chemical properties of the water are measured by various methods. The most accurate and precise methods to monitor sanitizer residuals use either an automated titration or an amperometric probe. Controllers that use these methods are more commonly used in drinking water and some pool and spa markets.

Oxidative Reduction Potential (ORP), which is a relatively inexpensive technique, has gained some acceptance in the United States pool and spa market, but has several drawbacks as a method to monitor and control the sanitizer levels. For example, ORP does not measure the "chlorine" or "bromine" sanitizer level directly, it measures the oxidative state of the water.

ORP readings are subject to interference from non-biocidal oxidizers and other chemicals commonly found in treated water. In that regard, ORP probe fouling often causes ORP readings to decrease even when the true ORP—or the true oxidative state—remains unchanged. Similarly, the ORP reading can decrease and the sanitizer levels would remain the same. Moreover, in treated water that uses isocyanurate such as trichloro-s-triazinetrione (trichlorisocyanuric acid or TCCA) or dichlorisocyanuic acid or dimethyl or methylethylhydantoins that have N,N-dibromo-, N,N-dichloro-, or N-N-bromochloro substituents, the problem seems to be exacerbated.

For example, in water that is treated with isocyanurate sanitizers it is not uncommon for the ORP reading to drop by 50–100 mV within a few days or a few weeks even if the true sanitizer level remains unchanged. The result is that a controller that is operating at a predetermined ORP set point (e.g. 650 mV) will continue to feed sanitizer causing the chlorine or bromine residual to exceed the range typically maintained.

In view of the above, it is well established that ORP probes must be cleaned to obtain a fast response and an accurate reading. However, to manually clean ORP probe surfaces is not practical in many applications since a knowledgeable technician is needed and strong acids are commonly used.

Accordingly, several different types of automatic cleaning systems have been developed in an attempt to reduce the cleaning requirements for ORP probes. These ORP probe cleaning systems have been used in certain large applications; but they are complicated, expensive and require a motor, an ultrasonic device, or cleaning supplies like compressed air, high-pressure water, or concentrated acids therefore unsuitable for smaller water treatment applications.

Regardless of the cleaning method, it is widely taught and practiced that the ORP probe metal surfaces should be allowed to stabilize at which time an oxidative film is formed on the metal surface. This stabilization time often takes several hours. As a result, it is commonly believed that the ORP metal surface should not be cleaned constantly because a stable ORP surface would not be achieved.

In addition to the above, it is also known that probe fouling is a significant problem for pH probes. As with ORP probes, the sensing surface of a pH probe must remain clean for accurate measurement. When the sensing surface is not clean, slow responses and inaccurate calibration may result.

A need therefore exists for a simple, cost effective way to keep ORP probes and/or pH probes clean when used to monitor recirculating water systems. The present invention addresses that need.

SUMMARY OF THE INVENTION

Briefly describing one aspect of the present invention, there is provided a self-cleaning probe system for monitoring, for example, the oxidation-reduction potential and/or the pH of a water system such as a swimming pool or spa. The self-cleaning probe system preferably comprises: (1) an ORP probe including an ORP electrode; (2) a flow cell; and (3) cleaning balls. The electrode portion of the probe is mounted within the flow cell, and the flow cell is connected to a water line so that the water to be monitored passes through the cell. A plurality of the cleaning balls are contained within the flow cell. When liquid flow is initiated, the cleaning balls become mobile within the flow cell, causing the balls to impinge on the surface of the electrode. That cleaning action keeps the surface of the electrode clean and ensures that the ORP probe provides accurate and stable ORP readings.

In a further embodiment the flow cell can accommodate a pH probe in addition to, or as an alternative to, the ORP probe.

One object of the present invention is to provide a self-cleaning ORP probe.

Other objects and advantages will be apparent from the following description.

DESCRIPTION OF THE PREFERRED EMBODIMENTS

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As indicated above, the present invention relates generally to electrochemical probes for use in water treated with oxidizing sanitizers, such as swimming pool or spa water. In one aspect of the invention there is provided a self-cleaning ORP probe for use in circulating water systems. The inventive ORP probe system is self-cleaning due to the action of glass or plastic or ceramic cleaning beads that are put in turbulent contact with the probe electrode surface. In another aspect of the invention there is provided a method of measuring ORP in treated water without waiting for the ORP probe to build an oxidation film on the outside of the probe.

In a further aspect of the present invention there is provided a self-cleaning pH probe system for use in circulating water systems.

Referring first to the drawings, FIGS. 1–7 show the present invention applied to an ORP probe system. Self-cleaning ORP probe system 10 includes an ORP probe 11 in a flow cell 12. ORP probe 11 includes an ORP electrode 13 and associated wiring. The probe, and more particularly the electrode, may take any of several shapes as described below. Flow cell 12 has an inlet 14 for passing fluid into the cell, and an outlet 15 for removing fluid from the cell. Preferably, ORP electrode 13 is positioned between inlet 14 and outlet 15 so that fluid flows evenly around the electrode. It is understood that normally the fluid will be sanitized water, such as swimming pool or spa water. Other water systems may, of course, also be monitored and controlled with the inventive ORP probe system.

A plurality of cleaning beads 17 is provided in the flow cell. In the most preferred embodiments the beads are spheres or balls, but other shapes may also be used. The beads are adequate in number and small enough in size to be moved by the turbulent flow of the fluid in the cell to contact and clean electrode 13. The beads should be hard enough to effectively clean the probe surface when used herein, yet soft enough to avoid damaging the probe.

As indicated above, in the most preferred embodiments self-cleaning probe system 10 includes a standard ORP probe positioned with its electrode end in the flow cell. The ideal metal for the ORP electrode is a pure noble metal, such as platinum or gold. However, since the metal surface is constantly polished by the cleaning balls, a less inert or less expensive metal may also be used.

A band shaped ORP electrode on a glass probe (see, e.g., FIGS. 1 and 5) is used in some preferred embodiments, although a coil shaped electrode (see, e.g., FIGS. 3 and 4) may alternatively be used. The coil shaped electrode is preferred for some applications since it is less susceptible to breakage by the cleaning balls.

As described in the Examples herein, a coil shape nickel ORP probe was tested and found to perform acceptably. In a freshly made pH 4 buffer and quinhydrone mixture (ORP standard, 260 mV), the nickel coil ORP probe reading was 255 mV, which indicated that nickel or some other less inert metal may be used to make a very inexpensive ORP probe for certain applications.

The flow cell contains the electrode end of the ORP probe, and provides a chamber for the fluid to be monitored to contact the electrode. The flow cell also contains the cleaning beads, and is designed such that the flowing water will force the cleaning beads (or other types of cleaning materials) to constantly scrub the ORP metal surface. This prevents the formation of contamination on the electrode surface.

The cleaning beads themselves are preferably glass or plastic balls that are about 0.5 to 5 (preferably 1–2, most preferably about 2) mm in diameter. Any balls or other shaped material or device which could be moved by the water flow through the cell could also be used for this cleaning system. The density, size, and hardness of the cleaning balls should be such that the surface of the probe is kept clean with minimal abrasion to the cell or enclosure.

The flow rate of fluid in and through the flow cell should be consistent with the requirements of the specific probe being used. Flow rate, flow dynamics and cleaning ball size and density must be such that sufficient mobility is obtained to result in cleaning balls contacting the probe surface to better maintain a clean surface. In some preferred embodiments, flow rates of between about 5 gal/hr. (gph) and about 50 gph are advantageously used.

The cleaning function of the self-cleaning ORP probe system is activated automatically by the water flow though the ORP flow cell. When the system is in use or the pump is on, the circulating water will force the cleaning balls to start moving in a circulating motion contacting the probe's metal sensing surface. This action of constantly scrubbing the metal surface minimizes the surface fouling (foreign material accumulating) problem.

By carefully combining different shapes and designs of the ORP probe, flow cell and cleaning ball, the self-cleaning ORP probe can be adapted to different water treatment applications for optimum cleaning efficiency and minimum maintenance.

The self-cleaning ORP probe system described herein maintains accuracy and precision in challenging situations like those containing cyanuric acid or hydantoins in the water. The cleaning method taught herein provides a simple cleaning process that eliminates the need for any mechanical moving parts. In addition, operator convenience is increased since manual cleaning is eliminated.

As indicated above, in a further aspect of the invention the probe system also or alternatively includes a self-cleaning pH probe. The self-cleaning pH probe uses a flow cell and cleaning beads in a manner similar to that described for the ORP probe. The pH probe electrode is disposed in a flow cell (which may be the same flow cell that also contains the ORP probe electrode) where cleaning beads agitated by water flowing through the cell contact and clean the electrode surface.

Figure 13:
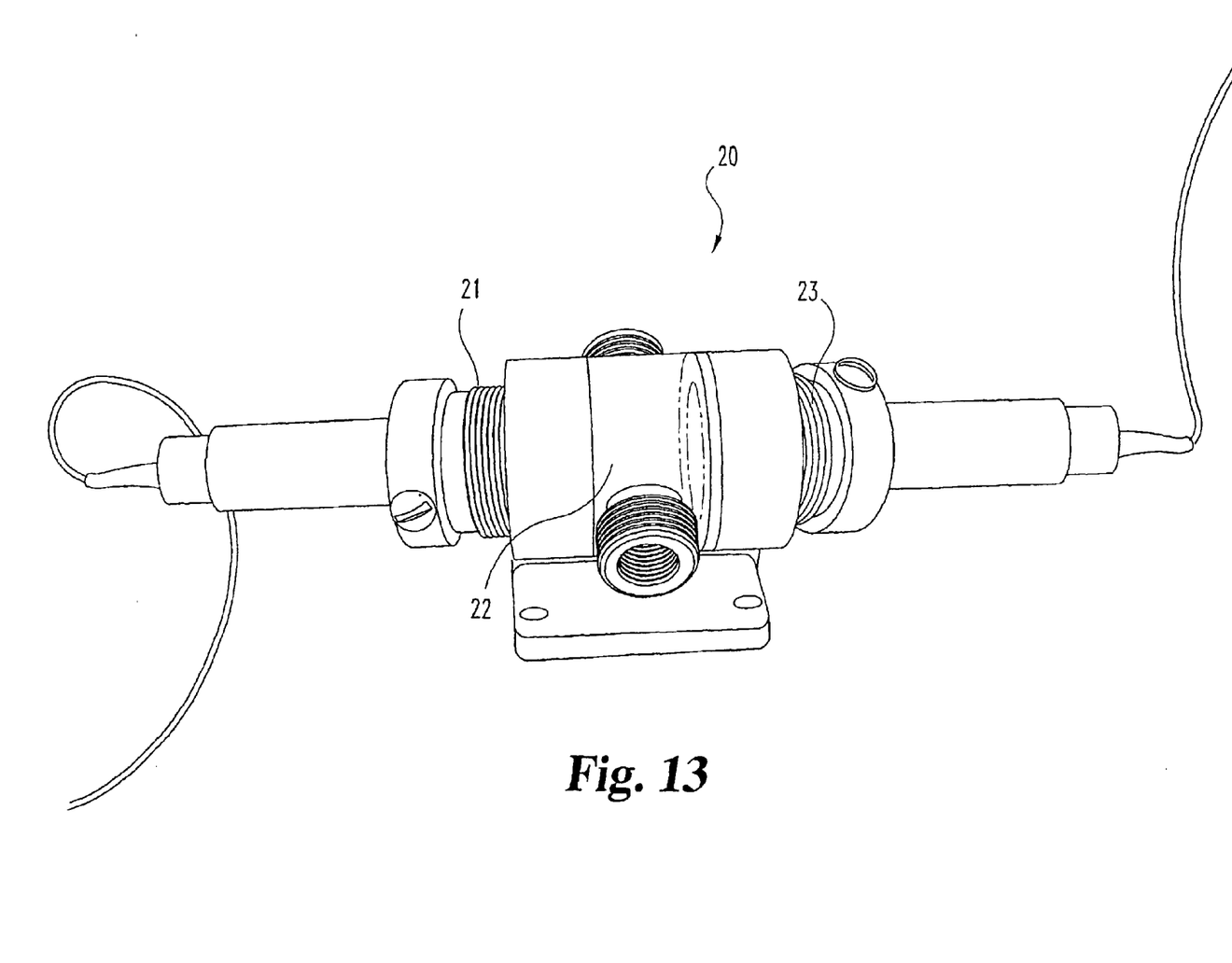
FIG. 13 shows a self-cleaning probe system including an ORP probe and a pH probe.

FIG. 13 shows one embodiment of the ORP/pH self-cleaning probe system. Probe system 20 includes ORP probe 21, flow cell 22, and pH probe 23. Cleaning beads as previously described are contained in flow cell 22.

Figure 14:
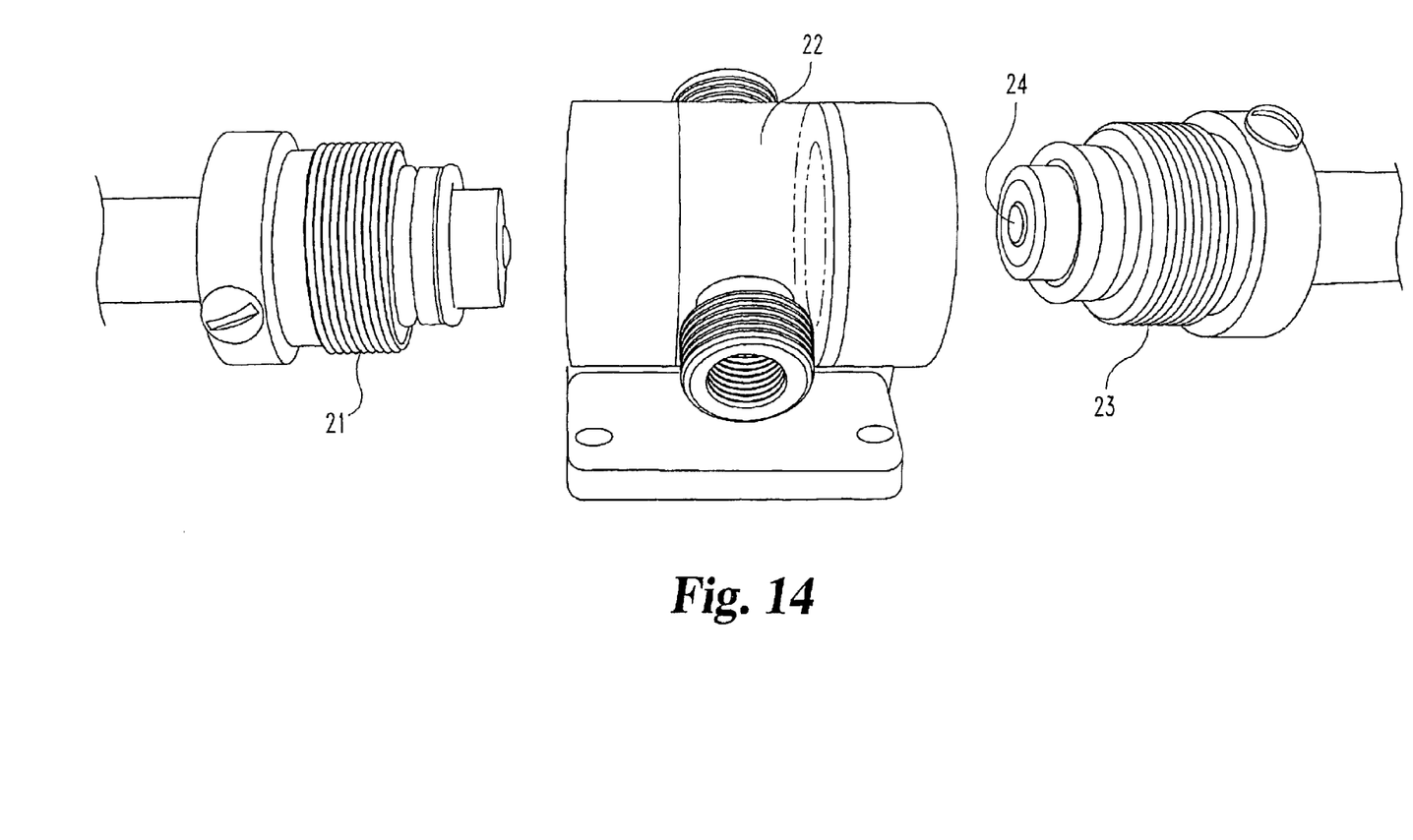
FIG. 14 shows the self-cleaning probe system of FIG. 13 with the ORP probe and the pH probe disengaged from the flow cell.
Figure 15:
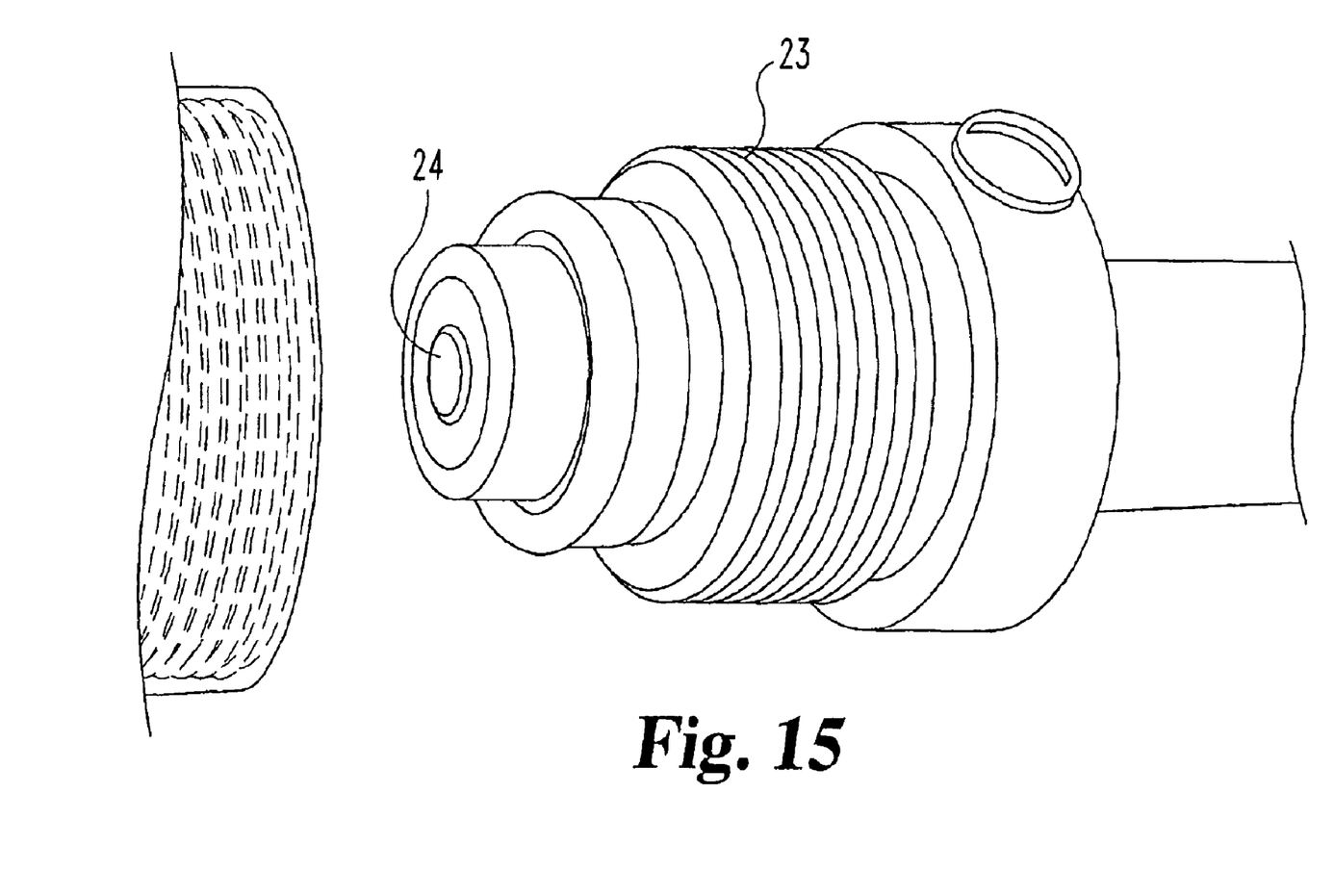
FIG. 15 shows the pH probe of the self-cleaning probe system of FIG. 13.

A pH electrode useful in the ORP/pH probe system is shown more clearly in FIG. 14. As shown in that Figure, the pH probe may have a flat electrode 24 that extends into the flow cell when the system is assembled. The electrode is cleaned by the agitated contact of the cleaning beads when water flows through the cell.

In a still further embodiment the self-cleaning probe system includes another fluid-testing probe, such as a temperature probe, etc., in addition to, or as an alternative to, the ORP and/or pH probes. The alternative fluid-testing probe is arranged so that the fluid testing portion is disposed in the flow cell where the action of cleaning beads agitated by water flow will contact and clean the fluid-testing portion.

In the most preferred embodiments the rate of water flow through the flow cell is controlled to maximize effective contact of the cleaning beads with the electrode surface(s). When the water flow is too slow, the cleaning beads are not agitated sufficiently to contact and clean the electrode(s). When the water flow is too fast, the cleaning beads are forced to the outside of the flow cell where they again fail to contact and clean the electrode. Water flow rates appropriate for a particular system can be determined by one skilled in the art without undue experimentation. For the systems tested to date, water flow rates of about 10 gal/hr provided effective agitation and cleaning.

Reference will now be made to specific examples using the processes described above. It is to be understood that the examples are provided to more completely describe preferred embodiments, and that no limitation to the scope of the invention is intended thereby.

TEST SYSTEM

A testing system including a 50 gallon polyethylene water tank, a recirculation pump capable of pumping water at 20 gal/min and a chlorinator containing TCCA was provided. Within the plumbing of the system, commercially available swimming pool probes were wired so that the ORP, pH and other readings were continuously monitored and downloaded into an electronic database. The ORP probes tested in Example 1 included: (A) Bayrol® Analyt 4 swimming pool controller with ORP (part #174040), pH (part #174030), Temperature (part #174050) probes encased in a manifold (part #174001); (B) Strantrol® System5 pool controller with ORP (part #7042003), pH (part #7040002), Temperature (part #000000) probes encased in a flow cell (part #1570008); and (C) ProMinent Dulcomarin® swimming pool controller with ORP (part #305097), amperometric CTE total chlorine probe (part #74684), pH (part #741036), and Temperature (part #305063) probes encased in a manifold (part #DGMA211T010).

The chlorine level of the tank was maintained at 3 ppm by a Prominent DULCOMARIN® controller with a total chlorine amperometric probe. When the chlorine level was below the set point, the chlorinator will proportionally turn on to feed TCCA to the set point.

Chlorine levels were verified with a HACH® DR/2000 spectrophotometer. Periodic samples were withdrawn from the water vessel and analyzed for free (DPD) and total (DPD) chlorine.

A Cole-Parmer Digi-Staltic® Modular Dispensing Pump was used to meter in 50 ml of sodium sulfite solution (5%) each hour. This addition of sodium sulfite solution is to lower the chlorine sanitizer level to less than 1.5 ppm to allow for the response of the ORP probe to be measured.

EXAMPLE 1

Using the system described above, the first test was performed for "uncleaned" ORP probes at a low level of CYA (15 ppm) in TCCA application.

The water vessel was filled with tap water and cyanuric acid was added to achieve a 15 ppm concentration. The water pH was maintained at 7.5 by adding 500 ml of 1M phosphate buffer. A 10N sodium hydroxide (NaOH) solution or 6 N hydrochloric acid (HCl) was used to adjust the pH to 7.5 as needed. Water was recirculated through the system for 5 days while the chlorine was maintained at 3 ppm.

The chlorine level was controlled at a set point of 3 ppm by Prominent DULCOMARIN® controller with a total chlorine amperometric probe as described above. The chlorine level was also verified by the DPD chlorine testing method using a HACH® DR/2000 spectrophotometer.

A sodium sulfite solution (5%) was contained in a addition chamber with a metering pump. The sodium sulfite solution was added to lower the chlorine sanitizer level to between 1.0 and 1.5 ppm to allow for the response of the ORP probe to be measured.

All three ORP probes used in this test were "uncleaned" ORP probes. They were running online more than 5 days without cleaning.

Figure 1:
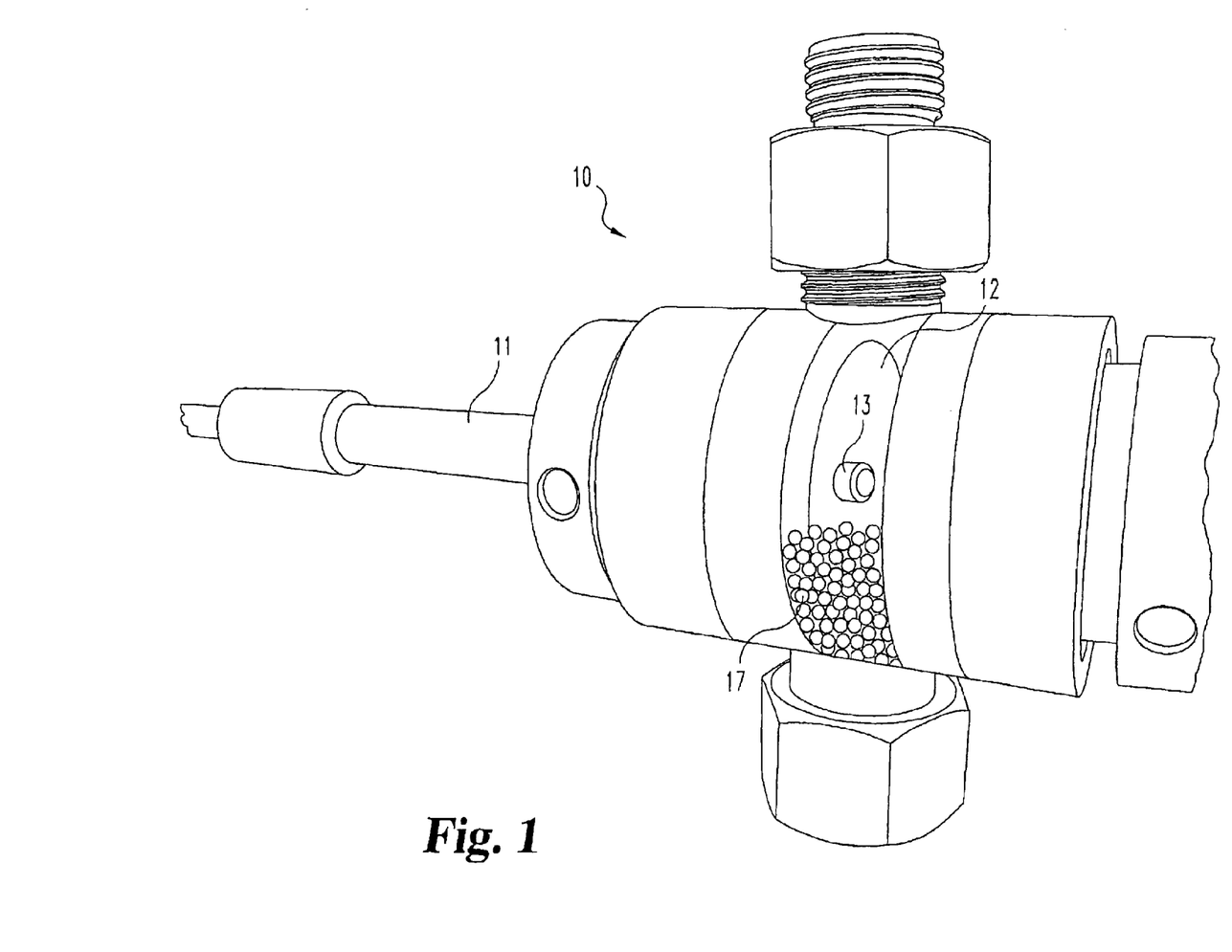
FIG. 1 shows a "band electrode" embodiment of the self-cleaning ORP probe of the present invention, with no water flowing through the device.
Figure 2:
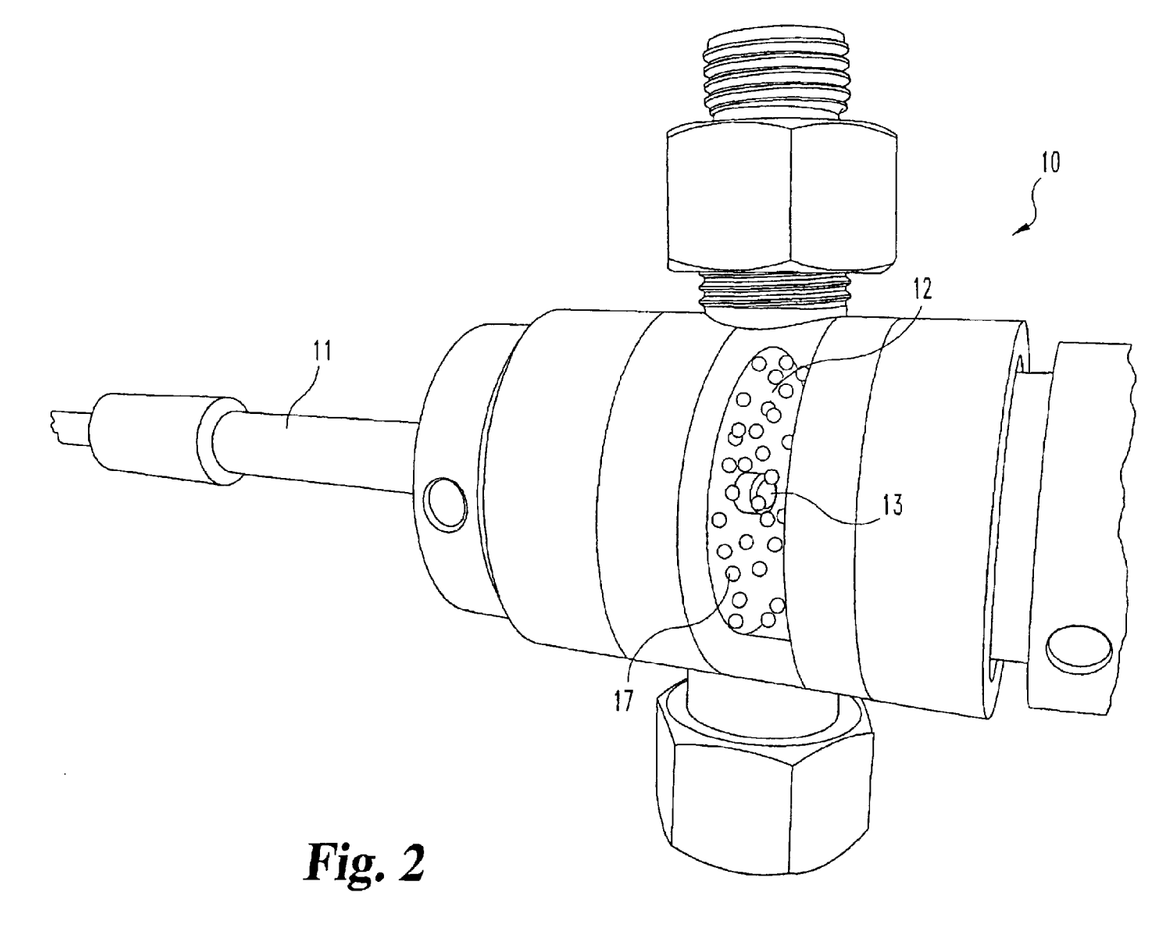
FIG. 2 shows the self-cleaning ORP probe of FIG. 1, with water flowing through the device.
Figure 3:
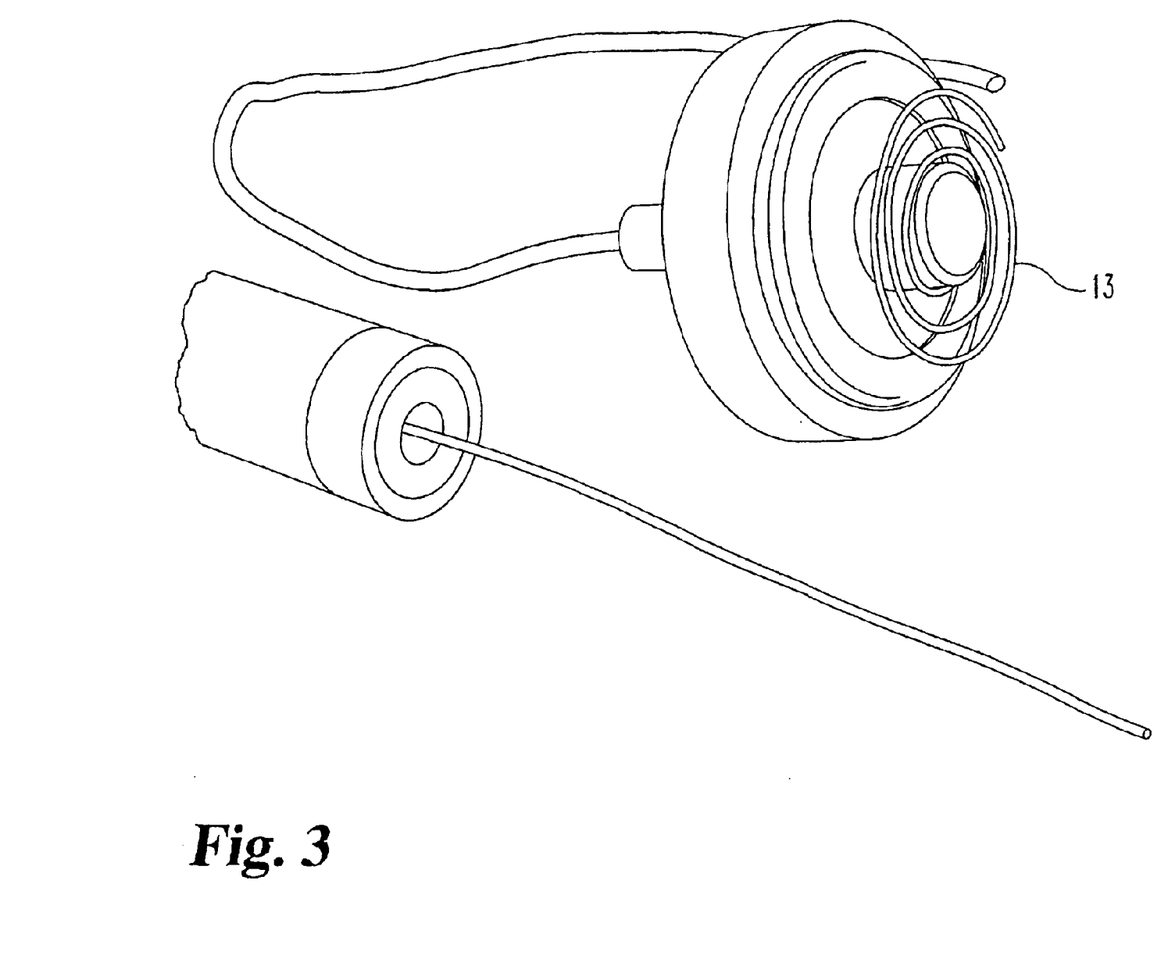
FIG. 3 shows a coiled electrode such as may be used in the self-cleaning ORP probe of the present invention.
Figure 4:
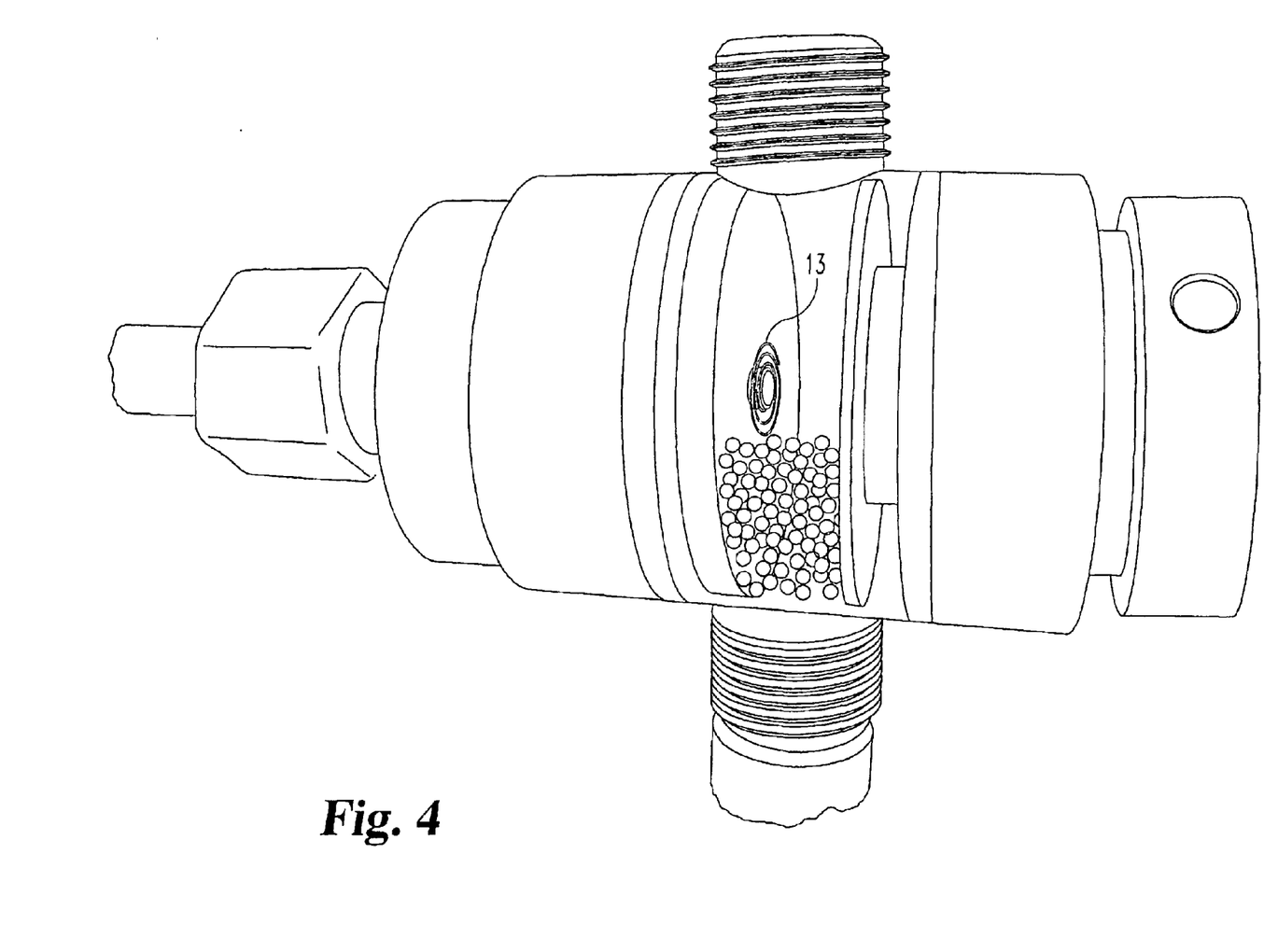
FIG. 4 shows a "coiled electrode" embodiment of the self-cleaning ORP probe of the present invention, with no water flowing through the device.
Figure 5:
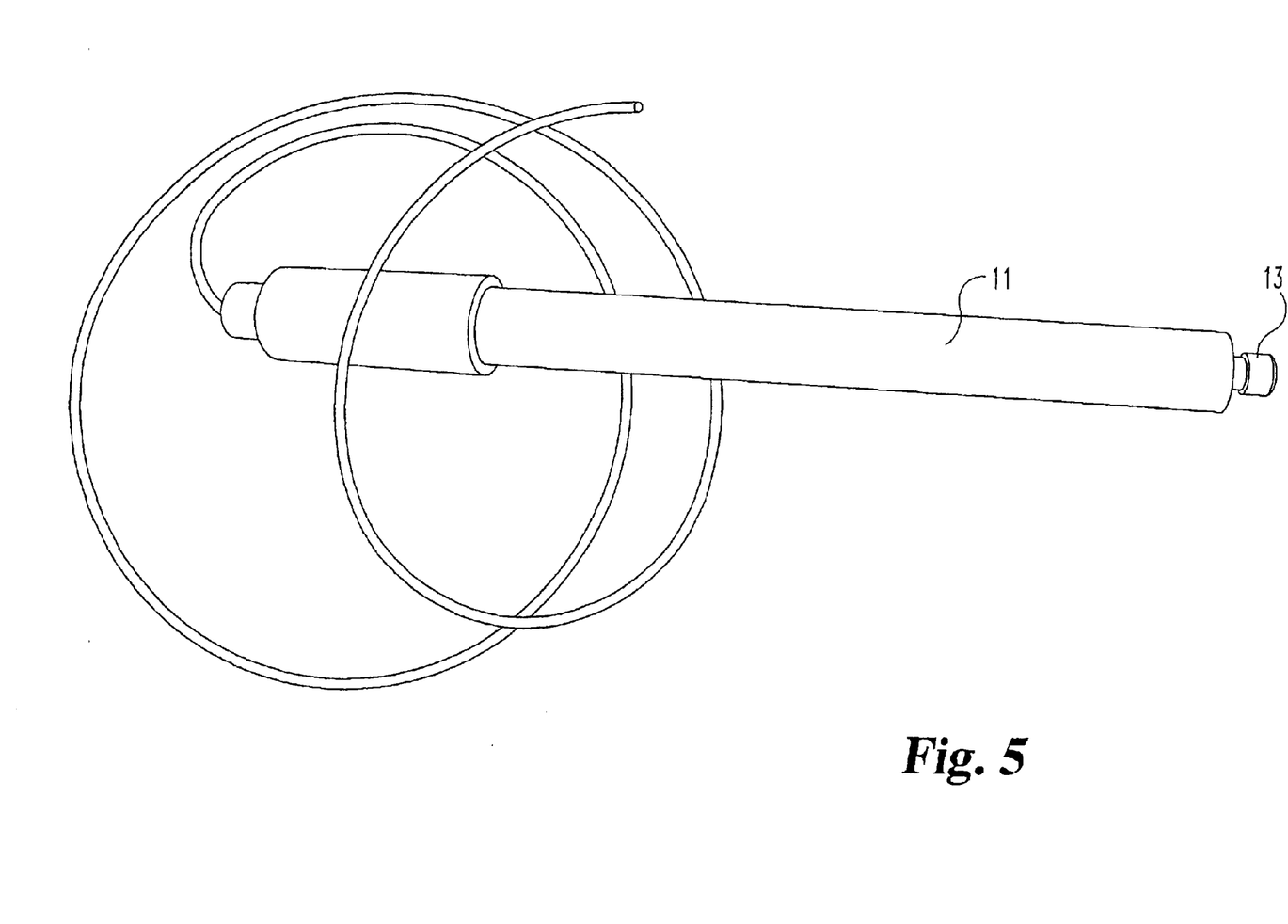
FIG. 5 shows a band electrode probe for use in the self-cleaning ORP probe of the present invention.
Figure 6:
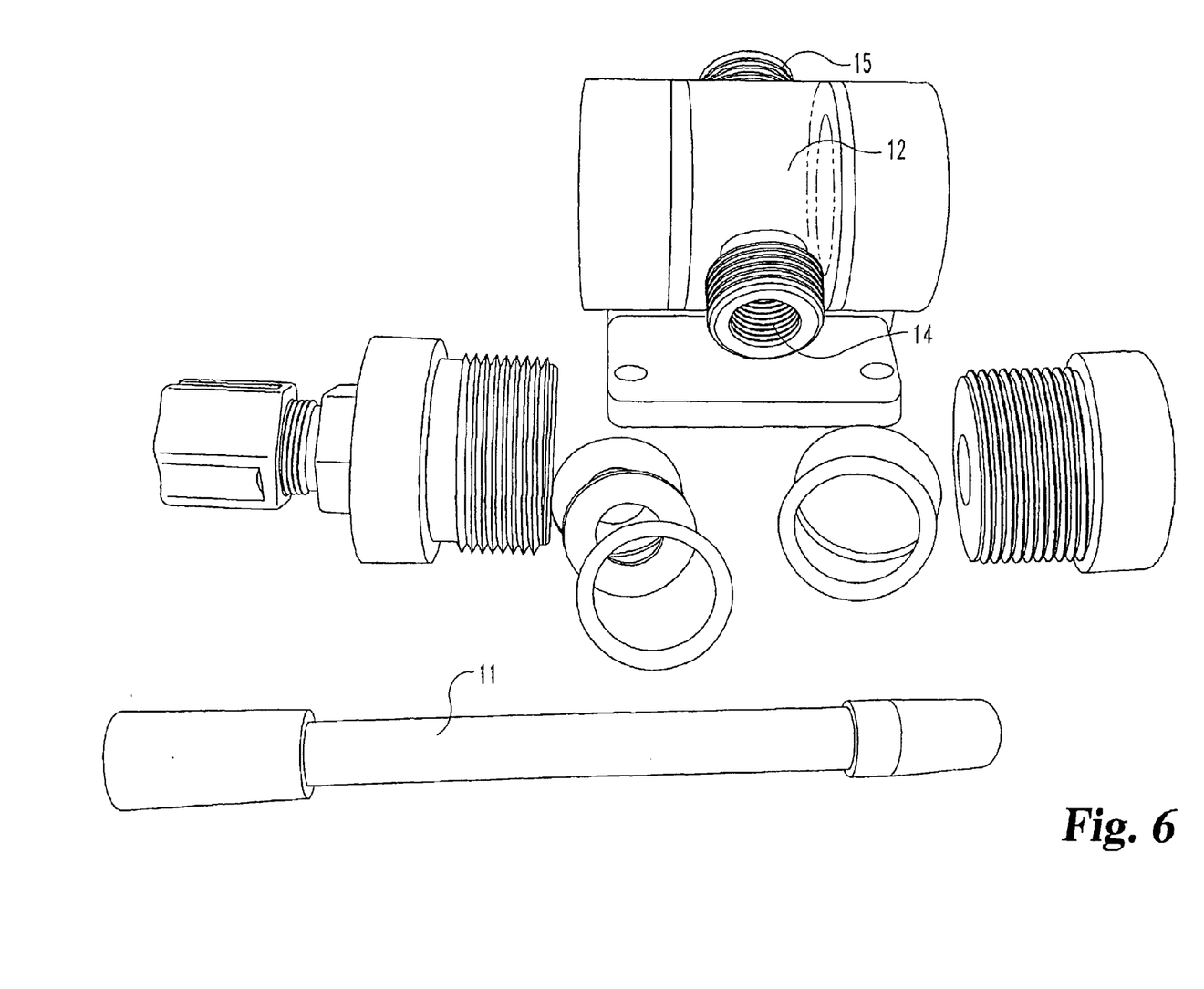
FIG. 6 shows the components of a "band electrode" embodiment of the self-cleaning ORP probe of the present invention.
Figure 7:
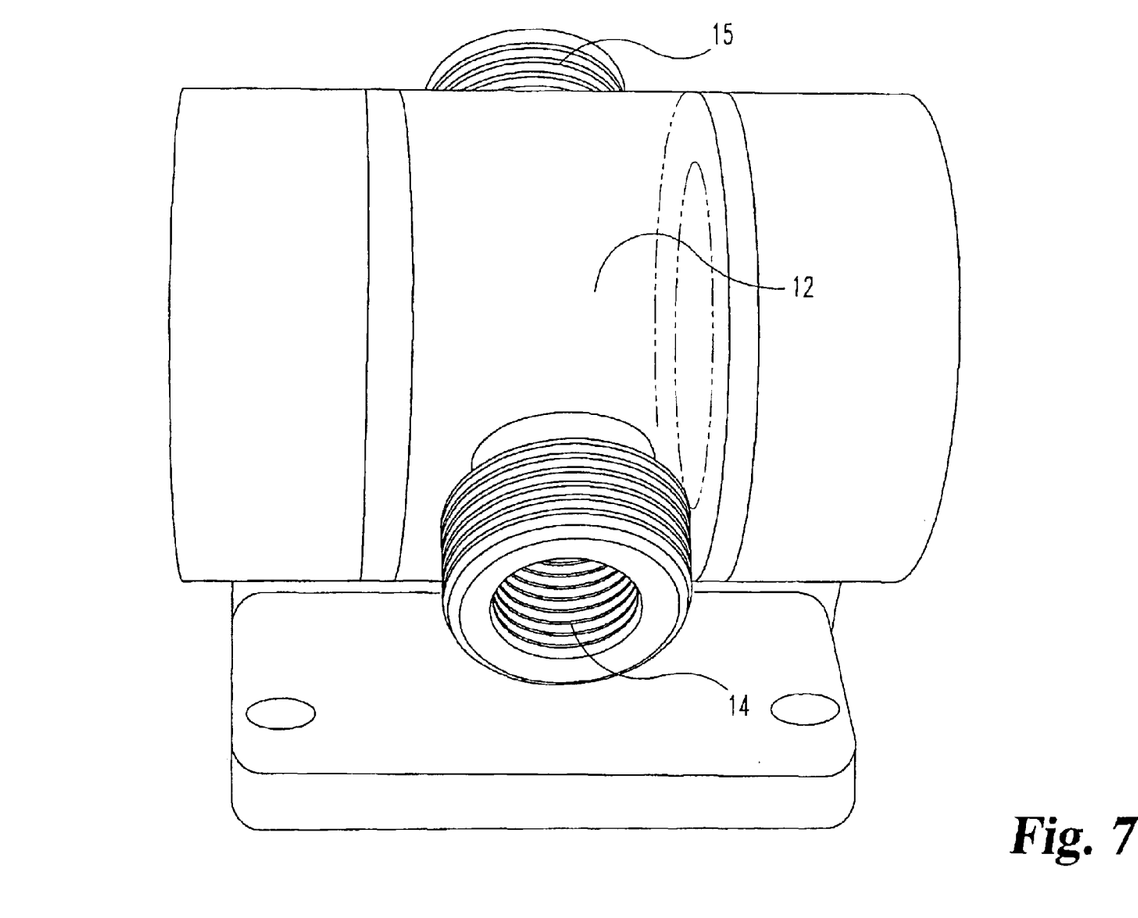
FIG. 7 shows the flow cell of the self-cleaning ORP probe of the present invention.
Figure 8:
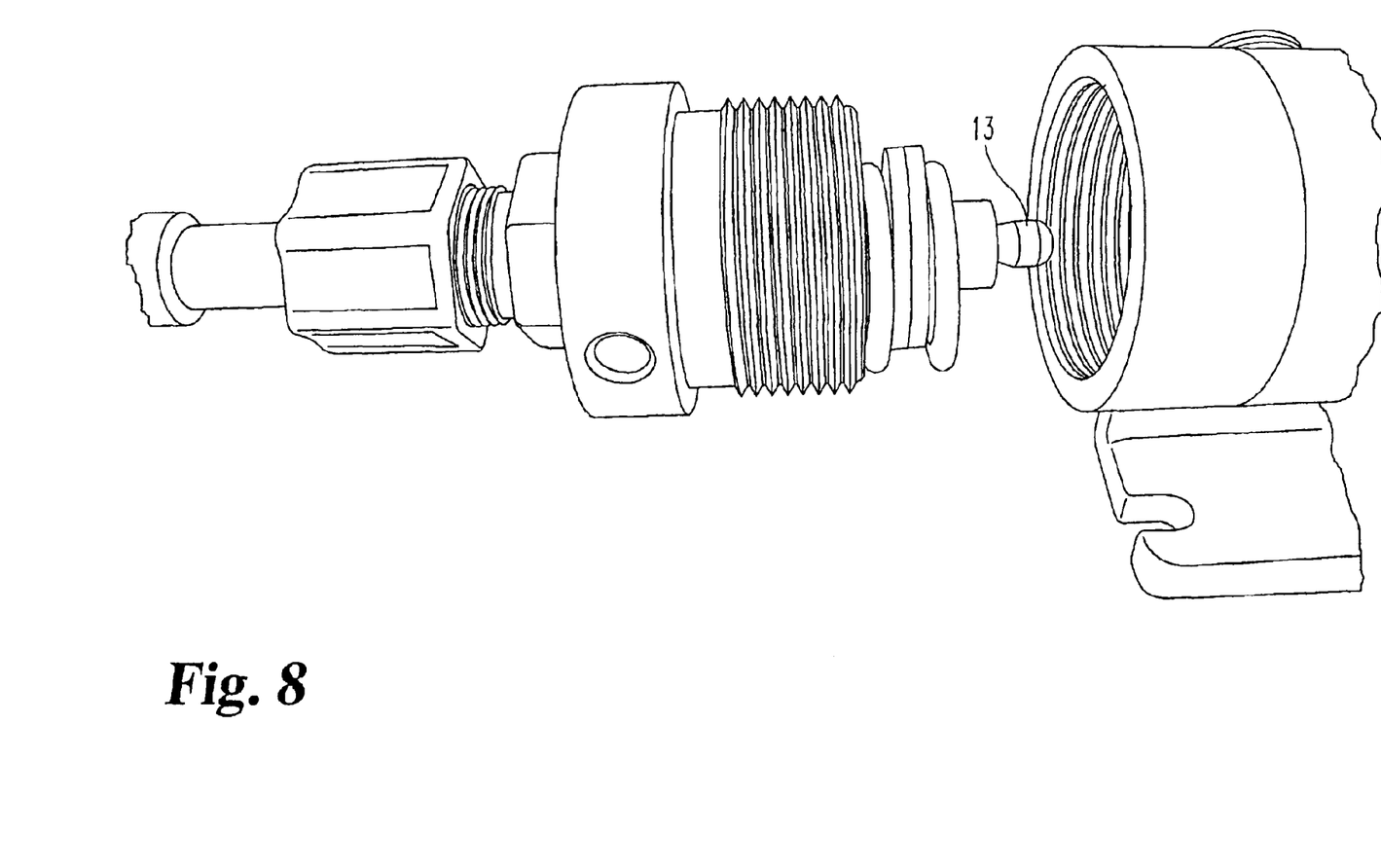
FIG. 8 shows a band electrode probe ready to install in the self-cleaning ORP probe of the present invention.
Figure 9:
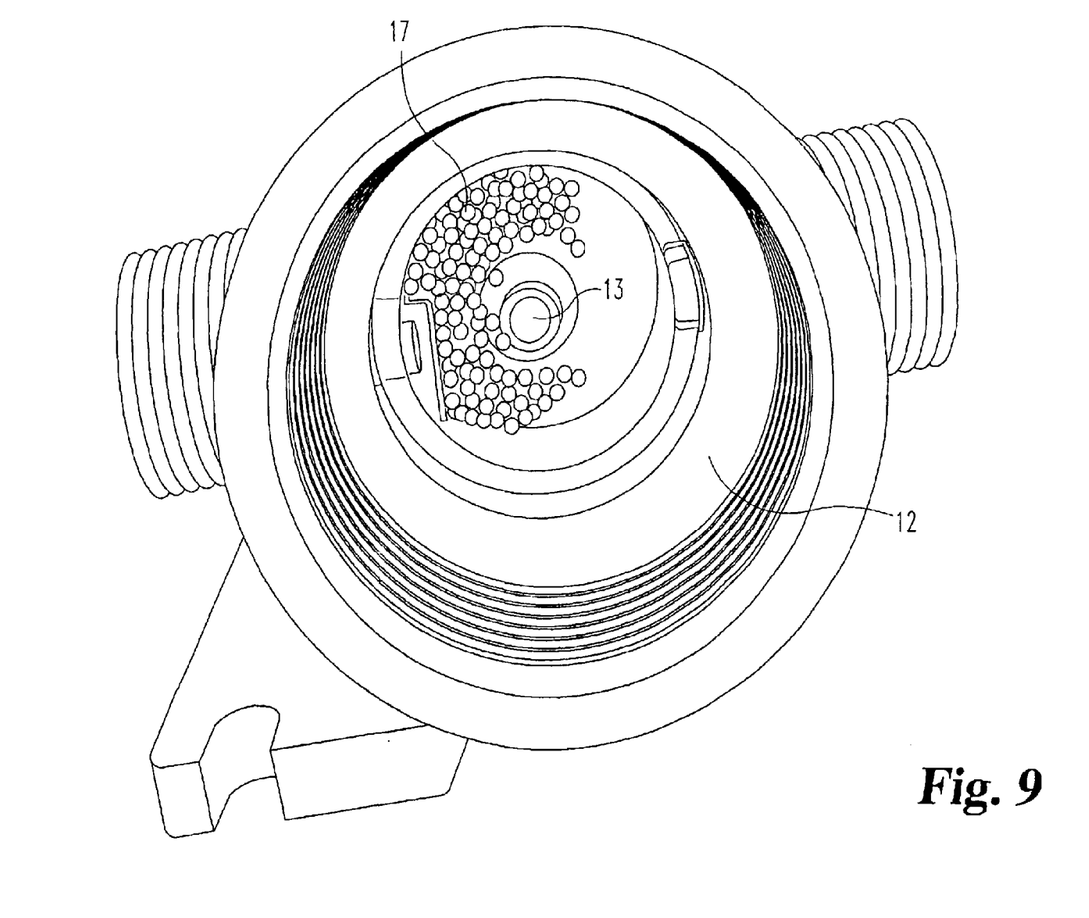
FIG. 9 shows the interior of the self-cleaning ORP probe of the present invention.
Figure 10:
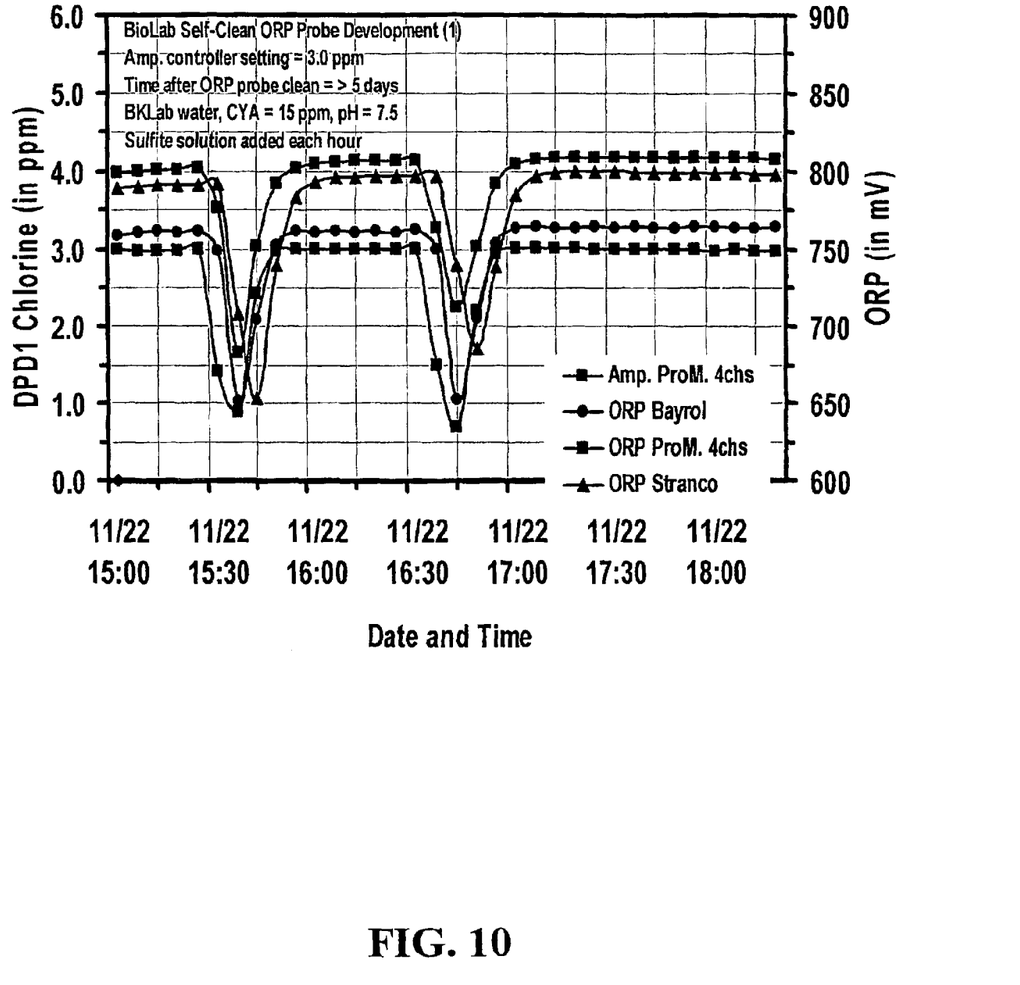
FIG. 10 is a graph showing ORP probe performance at low levels (15 ppm) of cyanuric acid.

The chlorine level in ppm (left axis and the line defined by "black square" data points) and the corresponding ORP readings in mV (right axis and the lines defined by the white data points) were recorded by computer datalog systems and they are plotted in FIG. 10.

FIG. 10 shows at the low levels of CYA application all ORP probes work well. The chlorine level (black square, Amp. ProM. 4Chs) was properly maintained at 3 ppm level. When 10 ml of 5% sulfite solution was added each hour, the chlorine level drops to about 1 ppm, and then goes back up to 3 ppm by automatically adding more TCCA in to the system.

The ORP readings from the three controllers, Bayrol® Analyt4 (ORP Bayrol), Dulcomarin® (ORP ProM. 4chs) and Strantrol® System5 (ORP Stranco), show that response to chlorine change are reasonably large (about 100 mV) and quick (in minutes). Therefore, without any other interferences, use of conventional on-line ORP probes without frequently cleaning for low level CYA gives consistent results.

EXAMPLE 2

Using the testing system described above, a test was designed to determine the effect of high level CYA (>200 ppm) on "uncleaned" ORP probes. These ORP probes were running online about 5 days without cleaning.

The water vessel was filled with tap water and cyanuric acid was added to achieve 250 ppm concentration. The water pH was maintained at 7.5 by adding 500 ml of 1M phosphate buffer. A 10N sodium hydroxide (NaOH) solution or 6 N hydrochloric acid (HCl) was used to adjust the pH to 7.5 as needed. Water was recirculated through the system for 5 days while the chlorine was maintained at 3 ppm.

The chlorine level was controlled at a set point of 3 ppm by Prominent DULCOMARIN® controller with a total chlorine amperometric probe. The chlorine level was also verified by the DPD chlorine testing method using a HACH® DR/2000 spectrophotometer.

A sodium sulfite solution (5%) was contained in an addition chamber with a metering pump. The sodium sulfite solution was added to lower the chlorine sanitizer level to about 1.0 ppm to allow for the response of the ORP probe to be measured.

Figure 11:
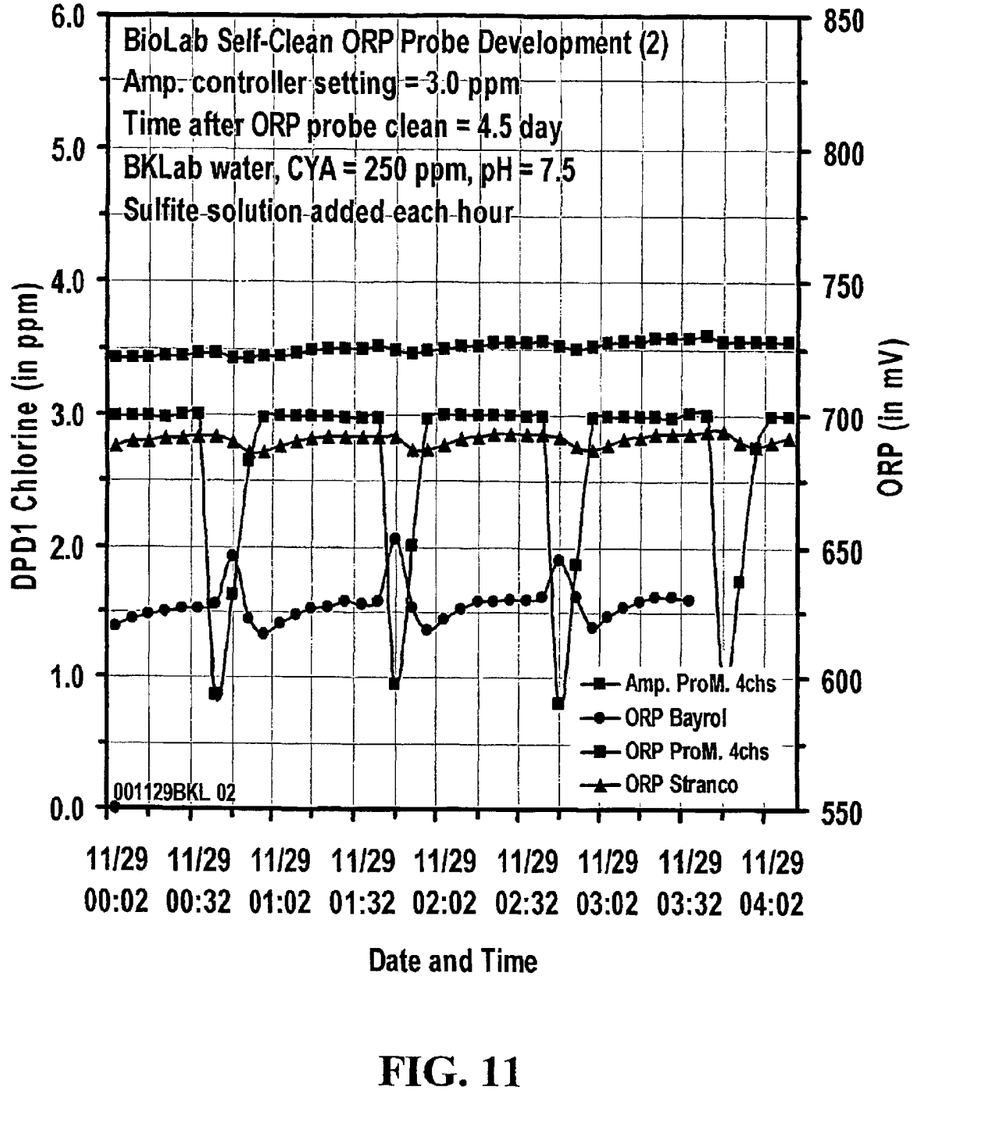
FIG. 11 is a graph showing ORP probe performance at higher levels (250 ppm) of cyanuric acid, 4.5 days after cleaning.

The chlorine level in ppm (left axis and the line defined by "black square" data points) and the corresponding ORP readings in mV (right axis and the lines defined by the white data points) were recorded by computer datalog systems and they are plotted in FIG. 11.

FIG. 11 shows that with high levels of CYA, and without frequent ORP probe cleaning, the ORP readings from the three controllers (ORP Bayrol, ORP ProM. 4chs, ORP Starnco) response to chlorine change are smaller (<20 mV), slower and erroneous. FIG. 11 also shows that at high levels of CYA, without daily cleaning, the ORP probe's reading decrease varies widely from one probe to another.

These test results demonstrated that due to the rapid ORP probe fouling, conventional on-line ORP probes may provide inaccurate ORP readings when CYA is present at high levels.

EXAMPLE 3

Using the testing system described above, a test was designed to determine the performance of probes made according to the present invention. High levels of CYA (>200 ppm) were used, and "clean" ORP probes were also tested to provide a baseline for comparison. The "clean" ORP probes were physically cleaned by 6N HCl about ½ day before the test. The self-cleaning ORP system was run more than 5 days without cleaning.

The water vessel was filled with tap water and cyanuric acid was added to achieve 250 ppm concentration. The water pH was maintained at 7.5 by adding 500 ml of 1M phosphate buffer. A 10N sodium hydroxide (NaOH) solution or 6 N hydrochloric acid (HCl) was used to adjust the pH to 7.5 as needed. Water was recirculated through the system for more than 5 days while the chlorine was maintained at 3 ppm.

The chlorine level was controlled at a set point of 3 ppm by Prominent DULCOMARIN® controller with a total chlorine amperometric probe. The chlorine level was also verified by the DPD chlorine testing method using a HACH® DR/2000 spectrophotometer.

A sodium sulfite solution (5%) was contained in an addition chamber with a metering pump. The sodium sulfite solution was added to lower the chlorine sanitizer level to about 1.5 ppm to allow for the response of the ORP probe to be measured.

The chlorine level in ppm (Amp. ProM. 4Chs) and the corresponding ORP readings in mV (ORP ProM. 4chs, ORP Stranco, ORP BiaLab New) were recorded by computer datalog systems and they are plotted in FIG. 12.

Figure 12:
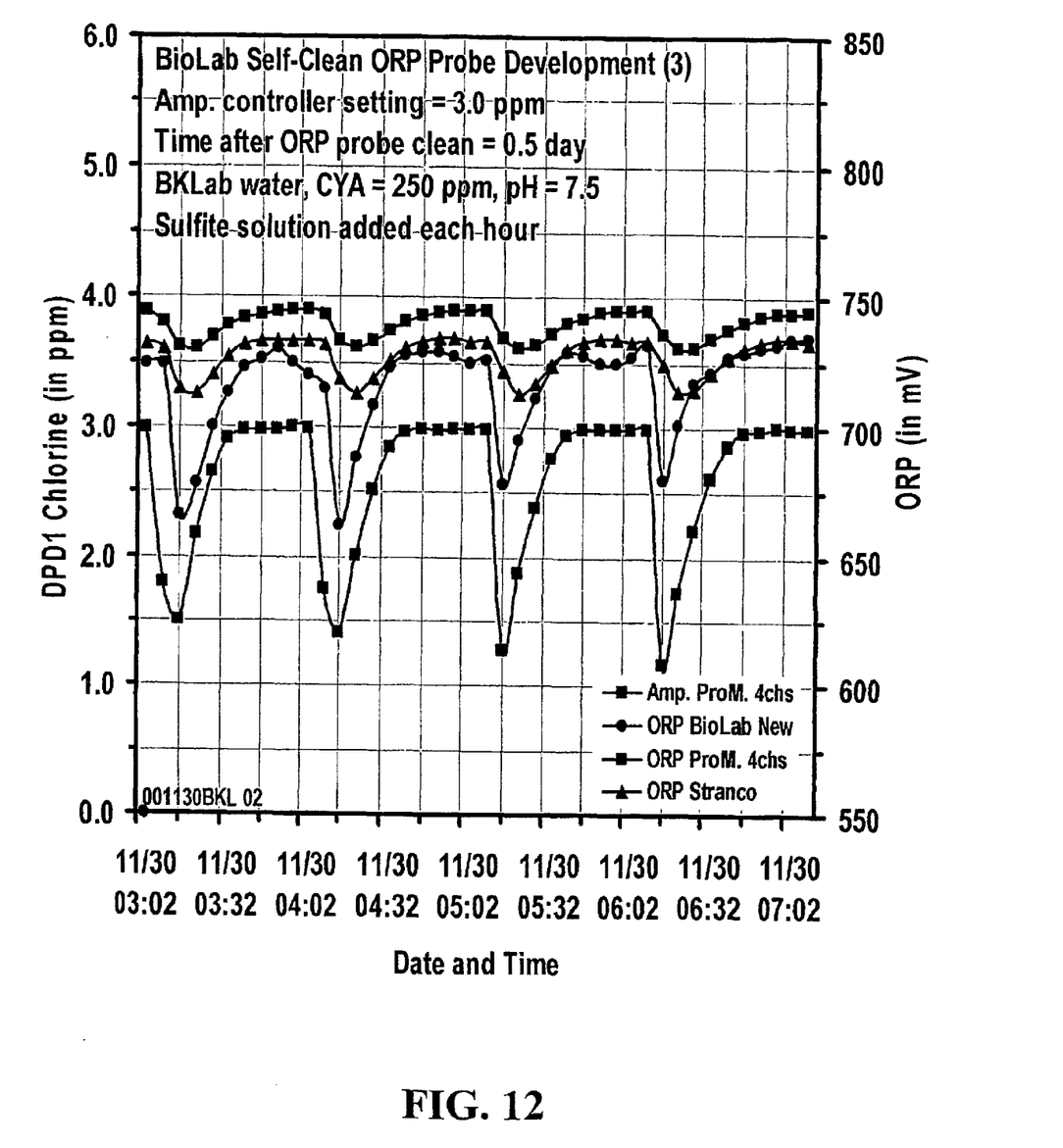
FIG. 12 is a graph showing the performance of the inventive self-cleaning ORP probe compared to other ORP probes at higher levels (250 ppm) of cyanuric acid, 0.5 days after cleaning.

FIG. 12 shows in the high CYA application, the clean ORP probes (ORP ProM. 4chs, ORP Stranco) are more sensitive to chlorine change than the "uncleaned" ORP probes (FIG. 11), but the responses, which are in the range of 10–20 mV, are still too small to be used safely for controlling swimming pools.

FIG. 12 also shows that the self-cleaning ORP probe system of the present invention (ORP BioLab New), running 5 days without manual cleaning, has the largest (about 50 mV) and the fastest response to the chlorine level changes.

This example demonstrated that with the inventive self-cleaning ORP probe the response of ORP probe to chlorine change in high level of CYA application (about 50 mV) is comparable to the low level CYA application (about 100 mV). The present invention provides a simple way to solve the ORP probe fouling problem and makes the ORP control of high level CYA pools possible.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A self-cleaning oxidation-reduction potential ("ORP") probe, comprising:
    (a) an ORP electrode;
    (b) a flow cell surrounding said ORP electrode, said flow cell including a fluid inlet for introducing fluid into the cell, and a fluid outlet for removing fluid from the cell; and
    (c) a plurality of cleaning beads contained in the flow cell in a manner in which they are free to contact the ORP electrode when fluid is passed through the cell.

2. The self-cleaning ORP probe of claim 1 wherein said ORP electrode is a metal band.

3. The self-cleaning ORP probe of claim 1 wherein said ORP electrode is a metal coil.

4. The self-cleaning ORP probe of claim 1 wherein said cleaning beads are balls with a diameter of between about 0.5 mm and 5 mm.

5. The self-cleaning ORP probe of claim 4 wherein said cleaning beads are balls with a diameter of between about 1 mm and 3 mm.

6. The self-cleaning ORP probe of claim 5 wherein said cleaning beads are balls with a diameter of about 2 mm.

7. The self-cleaning ORP probe of claim 1 wherein said cleaning beads are glass balls.

8. The self-cleaning ORP probe of claim 1 wherein said cleaning beads are plastic balls.

9. A method of measuring oxidation-reduction potential in a water system that is sanitized with between about 30 ppm and about 500 ppm of cyanuric acid or a cyanuric acid derivative, the method comprising using the ORP probe of claim 1 to accurately measure the oxidation-reduction potential of the water in the system.

10. A method of measuring oxidation-reduction potential in a system susceptible to ORP probe fouling, said method comprising using the ORP probe of claim 1 to accurately measure the oxidation-reduction potential of the water in the system.

11. A self-cleaning electrochemical probe system comprising:
    (a) an oxidation-reduction potential ("ORP") probe electrode;
    (b) a pH probe electrode;
    (c) a flow cell surrounding said ORP electrode and said pH electrode, said flow cell including a fluid inlet for introducing fluid into the cell, and a fluid outlet for removing fluid from the cell; and
    (d) a plurality of cleaning beads contained in the flow cell in a manner in which they are free to contact the ORP electrode and the pH electrode when fluid is passed through the cell.

12. A method of measuring the oxidation-reduction potential and the pH of water in a water system that is sanitized with between about 30 ppm and about 500 ppm of cyanuric acid or a cyanuric acid derivative, the method comprising using the ORP/pH probe system of claim 11 to accurately measure the oxidation-reduction potential of the water in the system.

* * * * *